(12) United States Patent
Desai et al.

(10) Patent No.: US 11,940,168 B2
(45) Date of Patent: Mar. 26, 2024

(54) DEVICE WITH OPTICAL HEART RATE SENSOR AND CORRESPONDING METHODS

(71) Applicant: Motorola Mobility LLC, Chicago, IL (US)

(72) Inventors: Rahul Bharat Desai, Hoffman Estates, IL (US); Amit Kumar Agrawal, Bangalore (IN)

(73) Assignee: Motorola Mobility LLC, Chicago, IL (US)

( * ) Notice: Subject to any disclaimer, the term of this patent is extended or adjusted under 35 U.S.C. 154(b) by 82 days.

(21) Appl. No.: 17/704,455

(22) Filed: Mar. 25, 2022

(65) Prior Publication Data

US 2023/0304695 A1    Sep. 28, 2023

(51) Int. Cl.

| | | |
|---|---|---|
| *F24F 11/80* | (2018.01) | |
| *A61B 5/00* | (2006.01) | |
| *A61B 5/024* | (2006.01) | |
| *F24F 11/56* | (2018.01) | |
| *F24F 11/66* | (2018.01) | |
| *F24F 11/67* | (2018.01) | |
| *F24F 120/20* | (2018.01) | |

(52) U.S. Cl.
CPC .............. *F24F 11/80* (2018.01); *A61B 5/004* (2013.01); *A61B 5/024* (2013.01); *F24F 11/56* (2018.01); *F24F 11/66* (2018.01); *F24F 11/67* (2018.01); *A61B 2560/0242* (2013.01); *A61B 2576/02* (2013.01); *F24F 2120/20* (2018.01)

(58) Field of Classification Search
CPC .. F24F 11/80; F24F 11/66; F24F 11/67; F24F 11/56
See application file for complete search history.

(56) References Cited

U.S. PATENT DOCUMENTS

| | | | |
|---|---|---|---|
| 9,750,420 B1* | 9/2017 | Agrawal | G06T 7/73 |
| 2012/0041278 A1* | 2/2012 | Sadhu | G08B 21/0446 600/301 |
| 2016/0061472 A1* | 3/2016 | Lee | F24F 11/64 700/276 |
| 2018/0231269 A1* | 8/2018 | Hiei | G16H 40/63 |
| 2019/0053713 A1 | 2/2019 | DeBates et al. | |
| 2019/0280890 A1* | 9/2019 | Muta | G06N 20/00 |
| 2020/0056797 A1* | 2/2020 | Tsujikawa | G05B 19/042 |
| 2020/0240670 A1* | 7/2020 | Kitagawa | F24F 11/30 |
| 2020/0352514 A1 | 11/2020 | Androulakis | |
| 2021/0153752 A1* | 5/2021 | Park | A61B 5/1176 |
| 2021/0215377 A1* | 7/2021 | Kitagawa | F24F 11/74 |
| 2021/0247078 A1* | 8/2021 | Nakagawa | E04B 2/7405 |

(Continued)

*Primary Examiner* — Nelson J Nieves
(74) *Attorney, Agent, or Firm* — Philip H. Burrus, IV

(57) ABSTRACT

An electronic device includes an image capture device that can be an always on image capture device. The electronic device includes one or more processors operable with the image capture device and a wireless communication circuit operable with the one or more processors. The one or more processors determine, from images of a face and torso of a user of the electronic device captured by the image capture device, that a heartrate of the user of the electronic device increases by a predetermined threshold above a resting level heartrate of the user of the electronic device. In response, the one or more processors cause the wireless communication circuit to transmit a climate adjustment request to a climate control device.

20 Claims, 8 Drawing Sheets

(56) References Cited

U.S. PATENT DOCUMENTS

| | | | |
|---|---|---|---|
| 2022/0065485 A1* | 3/2022 | Aoki | F24F 8/50 |
| 2022/0092331 A1* | 3/2022 | Stoppa | G06V 10/40 |
| 2022/0146335 A1* | 5/2022 | Uchiyama | A61B 5/01 |

* cited by examiner

DEVICE WITH OPTICAL HEART RATE SENSOR AND CORRESPONDING METHODS

BACKGROUND

Technical Field

This disclosure relates generally to electronic devices, and more particularly to wireless communication devices having image capture devices.

Background Art

Electronic devices, and in particular portable, wireless communication devices, are becoming increasingly technologically advanced. In response, users of such devices are employing the advance technology in increasingly interesting ways. Not too long ago, a mobile telephone was a luxury item used only for making voice calls. By contrast, people today rely upon smartphones and tablet computers to maintain their calendars, address books, music collections, photo collections, and so forth. Modern smartphones and other similar devices have evolved to the point that they serve as a computing device, entertainment device, productivity device, and communication device, all while neatly slipping into a pocket.

These smaller, yet more powerful, devices are being used for many different applications in many different environments. It would be advantageous to have new applications for electronic devices to detect certain environments offer enhanced performance within a given environment.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
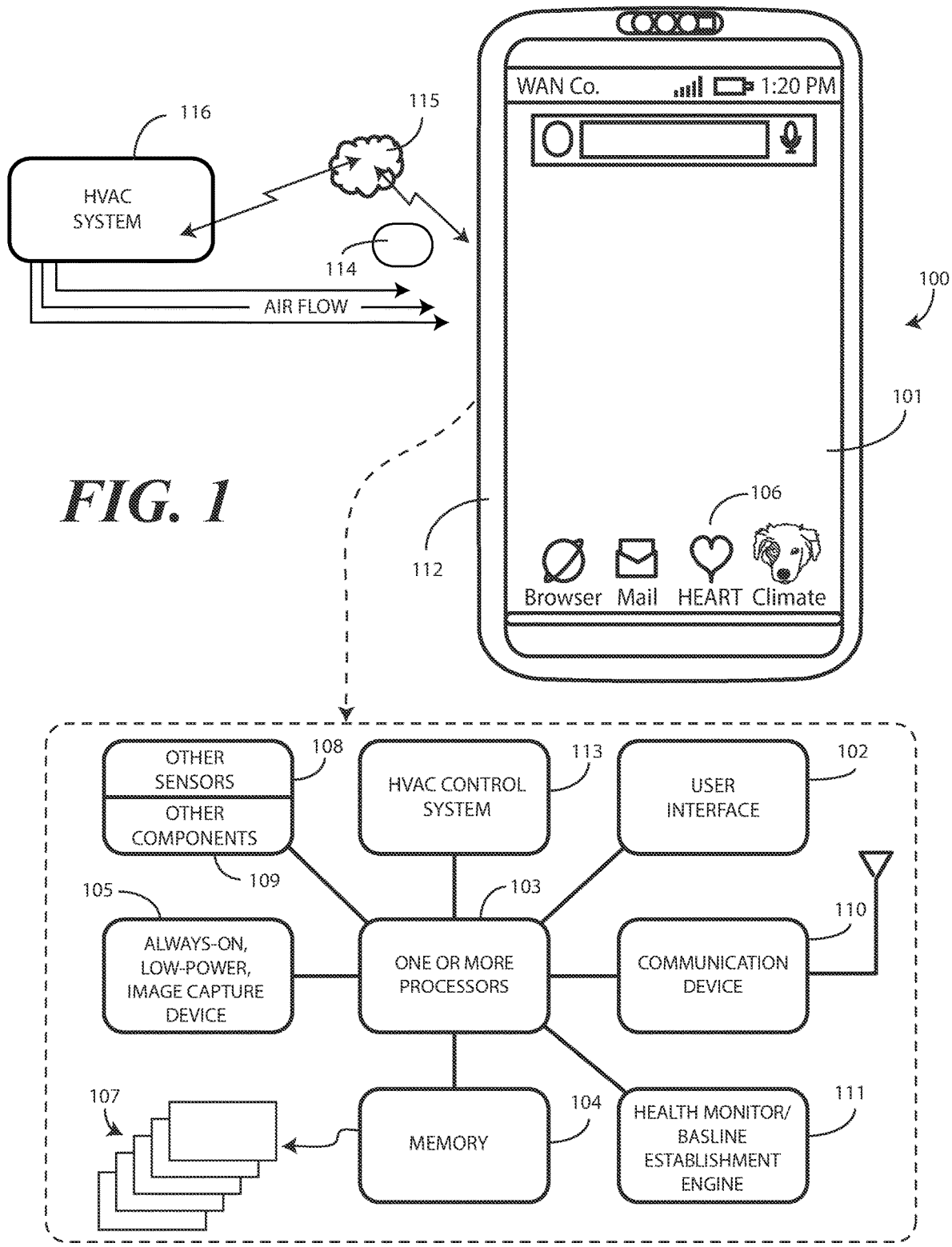
FIG. 1 illustrates one explanatory electronic device in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Before describing in detail embodiments that are in accordance with the present disclosure, it should be observed that the embodiments reside primarily in combinations of method steps and apparatus components related to optically sensing a heartrate of a user with an "always on" image capture device and then sending a climate adjustment signal to a remote climate control device or cooling system. Any process descriptions or blocks in flow charts should be understood as representing modules, segments, or portions of code that include one or more executable instructions for implementing specific logical functions or steps in the process.

Alternate implementations are included, and it will be clear that functions may be executed out of order from that shown or discussed, including substantially concurrently or in reverse order, depending on the functionality involved. Accordingly, the apparatus components and method steps have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Embodiments of the disclosure do not recite the implementation of any commonplace business method aimed at processing business information, nor do they apply a known business process to the particular technological environment of the Internet. Moreover, embodiments of the disclosure do not create or alter contractual relations using generic computer functions and conventional network operations. Quite to the contrary, embodiments of the disclosure employ methods that, when applied to electronic device and/or user interface technology, improve the functioning of the electronic device itself by and improving the overall user experience to overcome problems specifically arising in the realm of the technology associated with electronic device user interaction.

It will be appreciated that embodiments of the disclosure described herein may be comprised of one or more conventional processors and unique stored program instructions that control the one or more processors to implement, in conjunction with certain non-processor circuits, some, most, or all of the functions of optically detecting a heartrate of a user increasing by a predetermined threshold above a resting level heartrate baseline established via optical detection as well, actuation of a climate control system via the transmission of a climate adjustment request, and/or delivering messages to companion devices as described herein. The non-processor circuits may include, but are not limited to, a radio receiver, a radio transmitter, signal drivers, clock circuits, power source circuits, and user input devices. As such, these functions may be interpreted as steps of a method to perform controlling remote heating or cooling equipment in response to optically detected heartrates and their differences from an optically established resting heartrate baseline.

Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ASICs with minimal experimentation.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, components may be "operatively coupled" when information can be sent between such components, even though there may be one or more intermediate or intervening components between, or along the connection path. The terms "substantially," "essentially," "approximately," "about," or any other version thereof, are defined as being close to as understood by one of ordinary skill in the art, and in one non-limiting embodiment the term is defined to be within ten percent, in another embodiment within five percent, in another embodiment within one percent and in another embodiment within one-half percent. The term "coupled" as used herein is defined as connected, although not necessarily directly and not necessarily mechanically. Also, reference designators shown herein in parenthesis indicate components shown in a figure other than the one in discussion. For example, talking about a device (10) while discussing figure A would refer to an element, 10, shown in figure other than figure A.

Embodiments of the disclosure contemplate that the human body functions most efficiently within a fairly narrow temperature range having a mean of about 98.6 degrees Fahrenheit. Embodiments of the disclosure also contemplate that the human body's internal temperature sensor and temperature regulation mechanisms, for the most part, do a fairly good job of maintaining a constant body temperature. Illustrating by example, during exercise a person's breathing rate and heartrate increases when the body calls for more oxygen. The body also produces sweat, which in proper conditions evaporates from skin, thereby removing heat.

However, there are circumstances in which the body's internal mechanisms are less than effective. For instance, when a person sweats too excessively, there may be an insufficient amount of water remaining in the body to sufficiently cool the person. Similarly, in very humid environments the sweat may not evaporate sufficiently to remove the necessary heat to cool the skin. In cooler climates, the body may use its limited energy reserves to warm internal organs rather than the skin. In either condition, it is possible for a person's skin temperature to rise above, or fall below, a predefined skin temperature range that is optimal for health. When excessively high—or excessively low—skin temperature occurs, this can have adverse effects of human bodily function.

Embodiments of the disclosure work to resolve this problem by providing a device that includes an "always on" image capture device that monitors a user's heartrate by capturing one or more images of the user and analyzing those images to detect one or both of the user's heartrate and/or respiratory rate. Embodiments of the disclosure do this to use heartrate, and optionally respiratory rate, as a proxy for skin temperature. Advantageously, the use of the always on image capture device eliminates the need for the electronic device to include any skin temperature sensor.

Moreover, using the always on image capture device to optically monitor heartrate and/or respiratory rate means that the electronic device need not be in contact with the user's skin for accurate determinations of whether the user needs to be cooled or warmed with a climate control device. Accordingly, no headband, garment, or electronic device attached to the user is required. Instead, embodiments of the disclosure can be implemented in a smartphone, tablet computer, desktop computer, or other device without requiring any contact with the user's body.

In one or more embodiments, one or more processors determine from images of the face and torso of the user captured by an always on image capture device, that a heartrate of the user of the electronic device has increased by a predetermined threshold above a resting level heartrate. In one or more embodiments, the resting level heartrate is established by the electronic device using the always on image capture device as well.

In one or more embodiments, when the heartrate increases by a predetermined threshold above the resting level heartrate, one or more processors of the electronic device cause a wireless communication circuit to transmit a climate adjustment request to a climate control device. These operations take action to reduce the skin temperature as necessary. If the heartrate falls below the resting level heartrate, the one or more processors can take the opposite action to warm the user's skin, and so forth.

In one or more embodiments, an electronic device includes an "always on" image capture device that is operable to continuously measure a person's heartrate and/or respiratory rate. The image capture device is referred to as an "always on" image capture device because it is continually exposed in all geometric form factors of the electronic device and is continually active regardless of whether the electronic device is in an active mode of operation, a low-power mode of operation, or a sleep mode of operation. Said differently, the always on image capture device is not actively transitioned to a low-power or sleep mode to reduce overall sensor energy consumption. Instead, the always on image capture device draws currents less than a few milliamps when in operation in one or more embodiments.

By contrast, "high-power" sensors use large amounts of power when in operation. Accordingly, one or more processors of the electronic device actively transitions these sensors to a low power or sleep mode when not in use. Thus, they are the opposite of always on sensors in that they are generally turned OFF or put into a low power or sleep mode when not in operation. These sensors, which draw tens of milliamps to a few amperes, provide complex functionality. However, if left ON for long periods of time, these sensors will unnecessarily deplete energy stored in the battery, thereby reducing device run time. Examples of these high-power sensors include loudspeakers, high-resolution image capture devices, temperature sensors, touch sensors, high-resolution touch-sensitive displays, depth imagers, range scanners, force sensors, gaze detectors, and so forth.

Advantageously, embodiments of the disclosure rely solely on an always on image capture device to establish a resting level heartrate, detect a current heartrate, determine whether the current heartrate differs from the resting level heartrate by a predetermined threshold, and also determine a respiratory rate. This reduces power consumption due to the fact that no temperature sensor is required, thereby extending runtime of the electronic device. Moreover, even though the image capture device used to detect heartrate may be "always on," embodiments of the disclosure contemplate that there is processing overhead associated with the one or more processors and/or context engine ingesting and processing its output. Advantageously, in one or more embodiments the use of the always on image capture device is also minimized to determine whether heartrate of the user of the electronic device exceeds the resting level heartrate by a predetermined threshold to minimize this overhead, thereby further advantageously reducing power consumption by sensors in the electronic device and further extending runtime.

In one or more embodiments, the device also includes a wireless communication circuit configured to interact with remote "Internet of Things" devices, such as a heating ventilation and air conditioning (HVAC) system, fan, heater, or other climate control device. The wireless communication circuit can transmit climate adjustment requests to such a system to cool—or warm—the user as a function of the user's heartrate and/or respiratory rate.

In one or more embodiments, a method of using the electronic device comprises detecting, with an always on image capture device monitoring a user of the electronic device by capturing a plurality of successive images of the user of the electronic device, a heartrate of the user of the electronic device being above a predefined heartrate threshold. The method then comprises causing, with one or more processors when the heartrate of the user is above the predefined heartrate threshold, a wireless communication circuit to transmit a climate adjustment request to a climate control device. In one or more embodiments, the climate adjustment request requests that a temperature in an environment of the electronic device increase.

Embodiments of the disclosure contemplate that although temperature can be measured in absolute terms using a skin temperature sensor or other thermometer that must be in contact with a user's personage, the inherent "feeling" of temperature is a subjective human characteristic that is unique to each individual or condition. Despite the fact that Internet of Things climate control devices have become, they are not capable of detecting whether a user just returned from a workout and is feeling hot at the current temperature. Similarly, such climate control devices cannot determine if a user is feeling drowsy and needs a higher environmental temperature to feel comfortable.

To illustrating by example, consider the situation of a user who typically sets their HVAC system or climate control device to a home temperature of about seventy degrees Fahrenheit during the winter. This number may be the user's "comfortable ambient temperature" during the winter season in their home. However, what happens when the user returns from a brisk jog outside in the cold winter air? Generally speaking, the user will feel "hot" at this "comfortable ambient temperature" because of the physical activity just completed. Prior art climate control devices cannot detect this and cannot adjust the ambient temperature accordingly.

Advantageously, embodiments of the disclosure employ an always on image capture device that detects and measures a user's heartrate. One or more processors operable with the always on image capture device analyze the subtle changes in the shrinking and expanding of blood vessels in the face by measuring the color change of each pulse. The always on image capture device and one or more processors can do this while still offering power savings and with little impact to overall battery life of the electronic device.

Accordingly, in one or more embodiments one or more processors of an electronic device comprising an always on image capture device detect an environment where a wireless communication circuit of the electronic device is in communication with one or more Internet of Things HVAC systems or climate control devices. The always on image capture device then monitors—in a "touchless" manner without requiring any contact with the user—the user's face and torso. Using the always on image capture device, the one or more processors can continually track the user's resting level heartrate to establish a baseline. Respiratory rates can be monitored in a similar manner.

In one or more embodiments, in response to the one or more processors determining that the heartrate of the user has increased by a predetermined threshold above the resting level heartrate, the one or more processors cause the wireless communication circuit to send a climate adjustment request to an Internet of Things climate control device. In one or more embodiments, the climate adjustment request requests that the Internet of Things climate control device reduce the temperature of the environment of the user. In one or more embodiments, this decrease in temperature continues until the one or more processors cause the wireless communication circuit to send another climate adjustment request requesting the temperature return to the user's preferred normal level in response to the one or more processors determining the heartrate of the user has returned to within a predefined range of the resting level heartrate.

Embodiments of the disclosure can work in other ways as well. Illustrating by example, in response to the one or more processors determining that the heartrate of the user has decreased by a predetermined threshold below the resting level heartrate (these determinations can be made via machine learning across a predefined period of time), the one or more processors cause the wireless communication circuit to send another climate adjustment request to the climate control device to increase the ambient temperature. Embodiments of the disclosure contemplate that as a user becomes sleepy, the heartrate of the user will decrease to the lower end of a resting level heartrate range. However, in the process the user may initially feel colder since the heartrate of the user is pumping less blood throughout the body. Accordingly, embodiments of the disclosure can be used to warm the environment in addition to cooling.

The resting level heartrate and predefined thresholds at which climate adjustment requests are transmitted by the wireless communication circuit to the climate control device can be changed using a machine learning process that can occur across time. Advantageously, embodiments of the disclosure work to control an ambient temperature about a person via optically capturing images using an always on image capture device and without any contact between a sensor and the person being required. Embodiments of the disclosure dynamically and optically monitor a person's heartrate in real time (and optionally respiratory rate as well) to control a remote climate control device or HVAC system. Other advantages will be described below. Still others will be obvious to those of ordinary skill in the art having the benefit of this disclosure.

Turning now to FIG. 1, illustrated therein is one explanatory electronic device 100 configured in accordance with one or more embodiments of the disclosure. The electronic device 100 of FIG. 1 is a portable electronic device. For illustrative purposes, the electronic device 100 is shown as a smartphone. However, the electronic device 100 could be any number of other devices as well, including tablet computers, desktop computers, notebook computers, and so forth. Still other types of electronic devices can be configured in accordance with one or more embodiments of the disclosure as will be readily appreciated by those of ordinary skill in the art having the benefit of this disclosure.

This illustrative electronic device 100 includes a display 101, which may optionally be touch-sensitive. In one embodiment where the display 101 is touch-sensitive, the display 101 can serve as a primary user interface 102 of the electronic device 100. Users can deliver user input to the display 101 of such an embodiment by delivering touch input from a finger, stylus, or other objects disposed proximately with the display 101.

In one embodiment, the display 101 is configured as an active-matrix organic light emitting diode (AMOLED) display. However, it should be noted that other types of displays, including liquid crystal displays, would be obvious to those of ordinary skill in the art having the benefit of this disclosure. Where the electronic device 100 is configured with a keyboard and/or mouse, such as when the electronic device 100 is configured as a computer, the keyboard and/or mouse can serve as the primary user interface 102.

In one or more embodiments, the electronic device 100 includes a housing 112. The housing 112 can include one or more housing portions, such as a first housing portion and a second housing portion. In this illustrative embodiment, the housing 112 is disposed about the periphery of the display 101.

A block diagram schematic of the electronic device 100 is also shown in FIG. 1. The block diagram schematic can be configured as a printed circuit board assembly disposed within the device housing of the electronic device 100. Various components can be electrically coupled together by conductors or a bus disposed along one or more printed circuit boards.

In one or more embodiments, the electronic device 100 includes one or more processors 103. In one embodiment, the one or more processors 103 can include an application processor and, optionally, one or more auxiliary processors. One or both of the application processor or the auxiliary processor(s) can include one or more processors. One or both of the application processor or the auxiliary processor(s) can be a microprocessor, a group of processing components, one or more ASICs, programmable logic, or other type of processing device.

The application processor and the auxiliary processor(s) can be operable with the various components of the electronic device 100. Each of the application processor and the auxiliary processor(s) can be configured to process and execute executable software code to perform the various functions of the electronic device 100. A storage device, such as memory 104, can optionally store the executable software code used by the one or more processors 103 during operation.

The electronic device 100 also includes a wireless communication circuit 110 that can be configured for wired or wireless communication with one or more other devices or networks. The networks can include a wide area network, a local area network, and/or personal area network. The wireless communication circuit 110 may also utilize wireless technology for communication, such as, but are not limited to, peer-to-peer or ad hoc communications such as HomeRF, Bluetooth and IEEE 802.11, and other forms of wireless communication such as infrared technology. The wireless communication device 110 can include wireless communication circuitry, one of a receiver, a transmitter, or transceiver, and one or more antennas.

In one or more embodiments, the electronic device 100 includes an "always on" image capture device 105. In one embodiment, the always on image capture device 105 comprises a two-dimensional imager configured to receive at least one image of a person within an environment of the electronic device 100. In one embodiment, the always on image capture device 105 comprises a two-dimensional red-green-blue (RGB) imager. Other types of imagers suitable for use as the always on image capture device 105 of the electronic device 100 will be obvious to those of ordinary skill in the art having the benefit of this disclosure.

The always on image capture device 105 is operable to continuously measure a person's heartrate and/or respiratory rate. The always on image capture device 105 is "always on" because it is continually exposed in all geometric form factors of the electronic device (embodiments of the disclosure contemplate that its systems could also be implemented in a deformable electronic device such as one having a first device housing that is pivotable about a hinge relative to a second device housing between an axially displaced open position and a closed position) and is continually active regardless of whether the electronic device 100 is in an active mode of operation, a low-power mode of operation, or a sleep mode of operation. Said differently, the always on image capture device 105 is not actively transitioned to a low-power or sleep mode to reduce overall sensor energy consumption. Instead, the always on image capture device 105 draws currents less than a few milliamps when in operation in one or more embodiments.

In one embodiment, the one or more processors 103 can be responsible for performing the primary functions of the electronic device 100. For example, in one embodiment the one or more processors 103 comprise one or more circuits operable with one or more user interface devices, which can include the always on image capture device 105, to establish a resting level heartrate of a user—optionally using machine learning—by capturing a plurality of images of a user of the electronic device, determine a presently occurring heartrate of the user, and determined whether the presently occurring heartrate of the user differs from the resting level heartrate by more than a predetermined threshold. The executable software code used by the one or more processors 103, including that associated with a heartrate monitoring application 106 that utilizes the always on image capture device 105, can be configured as one or more modules 107 that are operable with the one or more processors 103. Such modules 107 can store instructions, control algorithms, logic steps, and so forth.

In one embodiment, the one or more processors 103 are responsible for running the operating system environment of the electronic device 100. The operating system environment can include a kernel and one or more drivers, and an application service layer, and an application layer. The operating system environment can be configured as executable code operating on one or more processors 103 or control circuits of the electronic device 100.

The application layer can be responsible for executing application service modules. The application service modules may support one or more applications or "apps," such as the heartrate monitoring application 106. The applications of the application layer can be configured as clients of the application service layer to communicate with services through application program interfaces (APIs), messages, events, or other inter-process communication interfaces. Where auxiliary processors are used, they can be used to execute input/output functions, actuate user feedback devices, and so forth.

In one embodiment, the one or more processors 103 may generate commands or execute control operations based upon user input received at the user interface 102. Moreover, the one or more processors 103 may process the received information alone or in combination with other data, such as the information stored in the memory 104.

The electronic device 100 can include one or more sensors 108. The one or more sensors 108 may include a microphone, an earpiece speaker, and/or a second loudspeaker. The one or more other sensors 108 may also include touch actuator selection sensors, proximity sensors, a touch pad sensor, a touch screen sensor, a capacitive touch sensor, and one or more switches. Touch sensors may used to indicate whether any of the user actuation targets present on the display 101, including the icon for the heartrate monitoring application 106, are being actuated. The other sensors 108 can also include audio sensors and video sensors (such as a camera).

The one or more sensors 108 can be configured to sense or determine physical parameters indicative of conditions in an environment about the electronic device 100. Illustrating by example, the one or more sensors 108 can include devices for determining information such as motion, bearing, location, acceleration, orientation, proximity to people and other objects, incident light amounts, and so forth. The one or more sensors 108 can include various combinations of microphones, location detectors, motion sensors, physical parameter sensors, barometers, proximity sensor components, proximity detector components, wellness sensors, touch sensors, cameras, audio capture devices, and so forth.

The one or more sensors 108 can also include a touch pad sensor, a touch screen sensor, a capacitive touch sensor, and one or more switches. The one or more sensors 108 can also include motion detectors, such as one or more accelerometers or gyroscopes. The motion detectors can detect movement, and direction of movement, of the electronic device 100 by a user. The one or more sensors 108 can also be used to detect gestures. For example, the other one or more sensors 108 can include one or more proximity sensors that detect the gesture of a user waving a hand above the display 101. In yet another embodiment, the accelerometer can detect gesture input from a user lifting, shaking, or otherwise deliberately moving the electronic device 100. It should be clear to those of ordinary skill in the art having the benefit of this disclosure that additional sensors can be included as well. Some of these components can be configured as Micro-Electro-Mechanical System (MEMS) sensors. Moreover, other types of sensors will be obvious to those of ordinary skill in the art having the benefit of this disclosure.

Other components 109 operable with the one or more processors 103 can include output components such as video outputs, audio outputs, and/or mechanical outputs. Examples of output components include audio outputs such as speaker port, earpiece speaker, or other alarms and/or buzzers and/or a mechanical output component such as vibrating or motion-based mechanisms. Still other components will be obvious to those of ordinary skill in the art having the benefit of this disclosure.

The other components 109 can also include an audio input/processor. The audio input/processor can include hardware, executable code, and speech monitor executable code in one embodiment. The audio input/processor can include, stored in memory 104, basic speech models, trained speech models, or other modules that are used by the audio input/processor to receive and identify voice commands that are received with audio input captured by an audio input/processor, one example of which is a microphone of the one or more sensors 108. In one embodiment, the audio input/processor can include a voice recognition engine. Regardless of the specific implementation utilized in the various embodiments, the audio input/processor can access various speech models to identify speech commands in one or more embodiments.

To establish a resting level heartrate using the always on image capture device 105, as well as detect a presently occurring heartrate of the user, in one or more embodiments the electronic device includes a health monitor/heartrate baseline establishment engine 111. In one or more embodiments, the health monitor/heartrate baseline establishment engine 111 receives signals from the always on image capture device 105 and analyzes the subtle changes in the shrinking and expanding of blood vessels in the face by measuring the color change of each pulse. The health monitor/heartrate baseline establishment engine 111 can use machine learning processes to establish the resting level heartrate and/or presently occurring heartrate of the user as well. Illustrating by example, the health monitor/heartrate baseline establishment engine 111 can establish, adjust, and improve the accuracy of the resting level heartrate and/or presently occurring heartrate of the user using machine learning over time and/or in response to user feedback delivered to the user interface 102. Accordingly, the health monitor/heartrate baseline establishment engine 111 receives the signals from the always on image capture device 105 to continually monitors—in a "touchless" manner without requiring any contact with the user—the user's face and torso. Using the always on image capture device 105, the health monitor/heartrate baseline establishment engine 111 continually track the user's resting level heartrate to establish a baseline. Respiratory rates can be monitored in a similar manner.

In one or more embodiments, the health monitor/heartrate baseline establishment engine 111 is operable with the one or more processors 103. In some embodiments, the one or more processors 103 can control the health monitor/heartrate baseline establishment engine 111. In other embodiments, the health monitor/heartrate baseline establishment engine 111 can operate independently, receiving signals or identifying heartrates from signals output by the always on image capture device 105. The health monitor/heartrate baseline establishment engine 111 can also receive data from the various sensors 108. In one or more embodiments, the one or more processors 103 are configured to perform the operations of the health monitor/heartrate baseline establishment engine 111.

The health monitor/heartrate baseline establishment engine 111 can be operable with the various sensors 108 to detect, infer, capture, and otherwise determine persons, actions, heartrates, respiratory rates, and other contextual information that are occurring with reference to a user present in an environment about the electronic device 100. These assessments may be learned through repetitive data analysis. These assessments can be used to obtain additional contextual information when the contextual information changes in one or more embodiments. The health monitor/heartrate baseline establishment engine 111 can comprise an artificial neural network or other similar technology in one or more embodiments.

The electronic device 100 can include a climate control device control system 113 operable to control a HVAC system or climate control device in communication with the wireless communication circuit 110. Illustrating by example, the climate control device control system 113 can generate climate adjustment requests when the health monitor/heartrate baseline establishment engine 111 determines that a heartrate of the user has deviated sufficiently from a resting level heartrate that the HVAC system or climate control device should alter an ambient temperature of an environment of the electronic device 100. The climate adjustment requests can include instructions or requests to increase the ambient temperature of the environment or reduce it as necessary, and so forth.

When the electronic device 100 is in action, the always on image capture device 105 can capture images of a face or torso of a user of the electronic device 100. The one or more processors 103 and/or health monitor/heartrate baseline establishment engine 111 can determine, from the images of the face or torso of the user, that a heartrate of the user of the electronic device increases by a predetermined threshold above a resting level heartrate of the user of the electronic device. In one or more embodiments, when this occurs, the one or more processors 103 and/or health monitor/heartrate baseline establishment engine 111 cause the wireless communication circuit 110 to transmit a climate adjustment request 114 across a network 115 to a climate control device 116 in communication with the wireless communication circuit 110. In one or more embodiments, such as when the user is exercising, the climate adjustment request comprises a request to reduce a temperature of the environment of the electronic device 100.

In one or more embodiments, the climate control device 116 comprises a fan. In another embodiment, the climate control device 116 comprises an air conditioner. In still other embodiments, the climate control device 116 comprises a heat pump. In yet other embodiments, the climate control device 116 comprises an air conditioning and furnace system. Other examples of climate control devices will be obvious to those of ordinary skill in the art having the benefit of this disclosure.

Embodiments of the disclosure contemplate that it is very important to maintain constant body temperature. If the user's body is unable to maintain a relatively constant temperature, the body can start functioning abnormally. Vigorous exercise for long duration causes increases in heart and breathing rates. In some situations, the body will send more energy to the muscles being exercised. Additionally, more rapid breathing increases the amount of thermal energy within the body. If the body does not have sufficient water to generate sweat, which evaporates, thereby removing heat, the body may keep increasing in temperature. Accordingly, embodiments of the disclosure contemplate that it can be important to track heartrate as a proxy for body temperature. Heartrate is advantageous to monitor over temperature because no contact with the user's skin is required. Embodiments of the disclosure contemplate that monitoring heartrate and/or respiratory rate is a very effective way to monitor body temperature.

Advantageously, while a user of the electronic device is exercising, the health monitor/heartrate baseline establishment engine 111 receives signals from the always on image capture device 105 and monitors the heartrate of the user to determine whether it is within an established resting level heartrate or is more than a predetermined threshold away from the resting level heartrate.

In one or more embodiments, the resting level heartrate is defined by a measured upper resting level heartrate average threshold and a measured lower resting level heartrate average threshold. Illustrating by example, the resting level heartrate may be between an upper resting level heartrate average threshold about one hundred beats per minute and a predefined lower resting level heartrate average threshold of about sixty beats per minute. This predefined resting level heartrate range is illustrative only. Other resting level heartrate ranges will be obvious to those of ordinary skill in the art having the benefit of this disclosure.

In one or more embodiments, where the one or more processors 103 and/or the health monitor/heartrate baseline establishment engine 111 determine, from signals received from the always on image capture device 105, that the currently occurring heartrate is outside the resting level heartrate range, the one or more processors 103 cause the wireless communication circuit 110 to transmit a climate adjustment request 114 to a climate control device 116.

Illustrating by example, presume a user is exercising in a room of her home. The environmental temperature is set by a climate control device 116, which in one embodiment is a HVAC system. In one or more embodiments, when the user's active heartrate rises more than a predetermined threshold above the measured upper resting level heartrate average, such as twenty beats per minute above the measured upper resting level heartrate average, the wireless communication circuit 110 of the electronic device 100 sends a message to the HVAC system requesting that the air conditioning be turned ON or down.

Once the currently occurring heartrate of the user falls back within the measured resting level heartrate range, in one or more embodiments a second climate adjustment request can be delivered to the climate control device 116 to deactivate the same and/or raise the temperature. The process can repeat should the heartrate of the user once again deviate from the resting level heartrate range.

It is to be understood that FIG. 1 is provided for illustrative purposes only and for illustrating components of one explanatory electronic device 100 in accordance with embodiments of the disclosure and is not intended to be a complete schematic diagram of the various components required for an electronic device. Therefore, other electronic devices in accordance with embodiments of the disclosure may include various other components not shown in FIG. 1 or may include a combination of two or more components or a division of a particular component into two or more separate components, and still be within the scope of the present disclosure.

Figure 2:
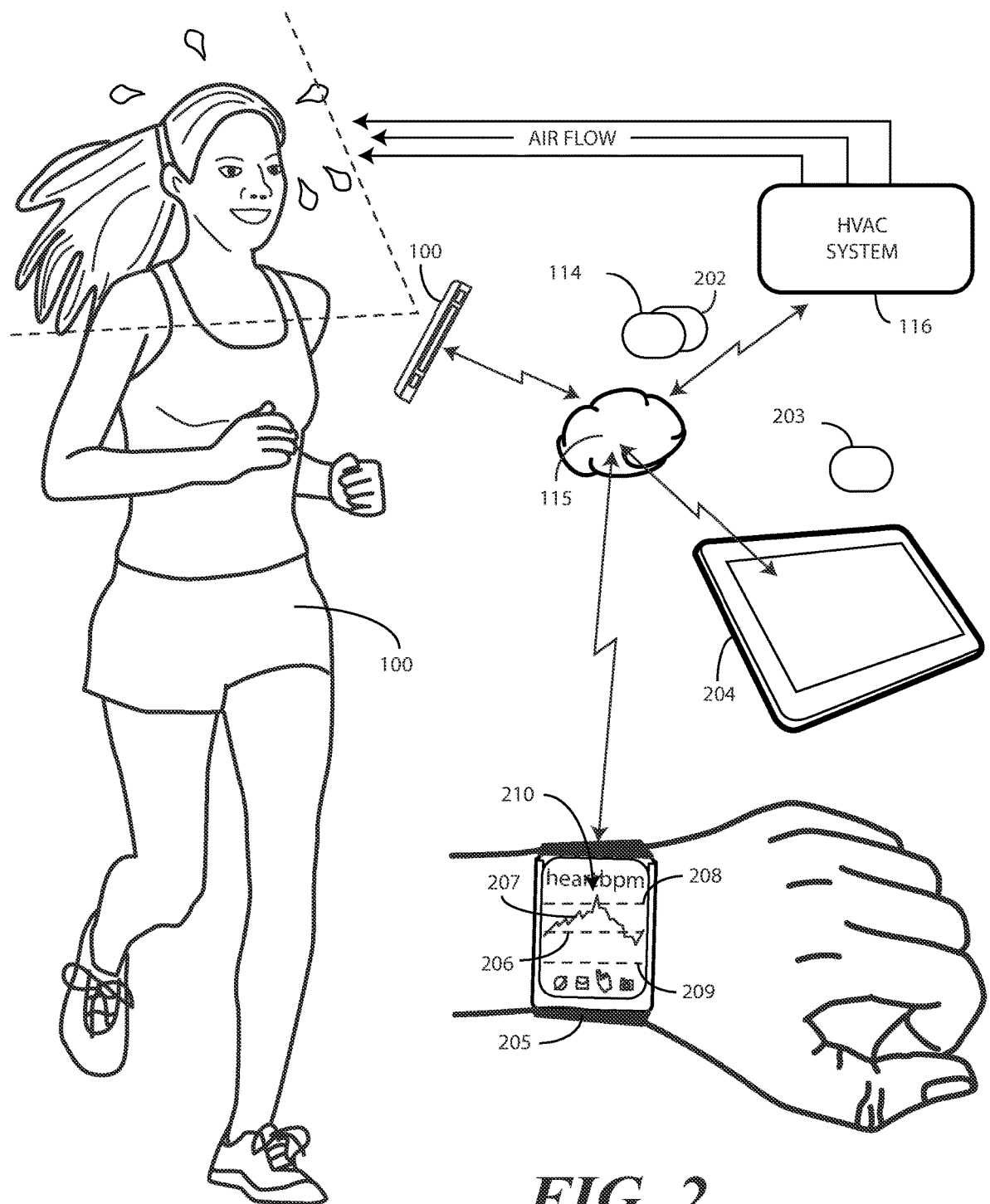
FIG. 2 illustrates one explanatory system in accordance with one or more embodiments of the disclosure.

Turning now to FIG. 2, illustrated therein is the electronic device 100 of FIG. 1 in use. As shown, a user 200 of the electronic device 100 is exercising. This exercise makes her heartrate rise.

As shown, the electronic device 100 is placed within a visible radius within which the always on image capture device (105) can monitor the user 200 of the electronic device 100 by capturing a plurality of successive images 201 of the user 200 of the electronic device 100. One or more processors (103) and/or a health monitor/heartrate baseline establishment engine (111) detect the heartrate of the user 200 of the electronic device 100 being above a predetermined heartrate threshold, one example of which is at least twenty beats per minute above a measured resting level heartrate determined by the one or more processors (103) and/or health monitor/heartrate baseline establishment engine (111).

When the one or more processors (103) and/or health monitor/heartrate baseline establishment engine (111) determine that the heartrate of the user 200 of the electronic device 100 is above the predefined heartrate threshold, in one or more embodiments the one or more processors (103) cause a wireless communication circuit (110) to transmit a climate adjustment request 114 to a climate control device 116. In one or more embodiments, the climate adjustment request 114 requests that a temperature of an environment of the electronic device 100 decrease.

Should the one or more processors (103) and/or health monitor/heartrate baseline establishment engine (111) determine that the heartrate falls back into the resting level heartrate range and/or below the resting level heartrate range by a predetermined threshold, the opposite can occur. Illustrating by example, if the user 200 of the electronic device 100 stops exercising, and the one or more processors (103) and/or health monitor/heartrate baseline establishment engine (111) determine from the signals received from the always on image capture device (105) monitoring the user 200 of the electronic device 100 that her heartrate falls to the resting level heartrate, the one or more processors (103) can cause the wireless communication circuit (110) to transmit another climate adjustment request 202 to the climate control device 116. In one or more embodiments, the other climate adjustment request 202 request that the climate control device 116 return the temperature of the environment of the electronic device 100 return to a level existing before the one or more processors (103) cause the initial climate adjustment request 114 to be transmitted. Alternatively, the other climate adjustment request 202 can comprise a request for the climate control device 116 to increase the temperature of the environment of the electronic device 100.

One advantage of using the always on image capture device (105) to monitor the user 200 of the electronic device 100 is that the images 201 of the face and torso of the user 200 of the electronic device 100 can be captured by the always on image capture device (105) while the electronic device 100 is in a low-power or sleep mode. Accordingly, one or more processors (103) and wireless communication circuit (110) and other components of the electronic device 100 can be placed in a low-power or sleep mode while the health monitor/heartrate baseline establishment engine (111) monitors signals received from the always on image capture device (105). When the health monitor/heartrate baseline establishment engine (111) determines that the heartrate of the user 200 of the electronic device 100 exceeds the resting level heartrate by a predetermined threshold and/or increase above a predefined heartrate threshold, the health monitor/heartrate baseline establishment engine (111) can cause the one or more processors (103) and wireless communication circuit (110) to transition from a low-power or sleep mode of operation to an active mode of operation to cause the climate adjustment request 114 to be transmitted to the climate control device 116, thereby saving power and extending run time of the electronic device 100.

Additionally, the one or more processors (103) and/or health monitor/heartrate baseline establishment engine (111) can further cause the wireless communication circuit (110) to deliver a heartrate elevation event message 203 across a network to a companion electronic device, examples of which include a tablet computer 204 and a smartwatch 205. Illustrating by example, the user 200 of the electronic device 100 may wish to record health information during exercise sessions in the companion electronic device. As such, in one or more embodiments when the heartrate moves outside the resting level heartrate by a predetermined threshold or above a predefined heartrate threshold, a heartrate elevation event message 203 indicating that this occurred is delivered to the companion electronic device. Additionally, in some embodiments the companion electronic device, rather than the electronic device 100 itself, can transmit the climate adjustment request 114 to the climate control device 116.

In the illustrative embodiment of FIG. 2, the one or more processors (103) of the electronic device 100 have caused the wireless communication circuit (110) to transmit both the resting level heartrate 206 and the heartrate 207 of the user 200 that is currently being measured to the smartwatch 205. Also shown on the display of the smartwatch 205 is an upper predefined heartrate threshold 208 representing a predetermined threshold above the resting level heartrate 206 and a lower predefined heartrate threshold 209 representing a predetermined threshold below the resting level heartrate 206.

In one or more embodiments, the one or more processors (103) and/or health monitor/heartrate baseline establishment engine (111) receive and analyze signals from the always on image capture device (105) across a period of time when the user 200 is not exercising to establish the resting level heartrate 206. In one or more embodiments, the resting level heartrate 206 is defined by a range spanning a certain number of beats per minute. Embodiments of the disclosure contemplate that the user 200 may experience a lower resting level heartrate 206 while sleeping than when sitting on the sofa watching television. Accordingly, and optionally using machine learning techniques, the one or more processors (103) and/or health monitor/heartrate baseline establishment engine (111) can establish a range defining the resting level heartrate 206 in one or more embodiments. In one or more embodiments, the range includes a mean and is bounded by the upper predefined heartrate threshold 208 and the lower predefined heartrate threshold 209. In one or more embodiments, the resting level heartrate range may be between an upper predefined heartrate threshold 208 of one hundred beats per minute and a lower predefined heartrate threshold 209 of sixty beats per minute. These heartrates may correspond to skin temperatures of 100.4 degrees Fahrenheit and ninety-seven degrees Fahrenheit, respectively. This heartrate limits are illustrative only. Of course, the mean, upper predefined heartrate threshold 208, and lower predefined heartrate threshold 209 will vary from user to user. Accordingly, other values for the resting level heartrate range will be obvious to those of ordinary skill in the art having the benefit of this disclosure.

When the user 200 is exercising, the one or more processors (103) and/or health monitor/heartrate baseline establishment engine (111) then monitor the heartrate 207 of the user 200 by analyzing images captured by the always on image capture device (105). In so doing, the one or more processors (103) and/or health monitor/heartrate baseline establishment engine (111) determine whether the heartrate 207 of the user 200 stays below the upper predefined heartrate threshold 208 and above the lower predefined heartrate threshold 209. When the heartrate 207 of the user 200 exceeds the upper predefined heartrate threshold 208 as it did at instance 210, the wireless communication circuit (110) of the electronic device 100 transmits the climate adjustment request 114 across the network 115 to the climate control device 116 to actuate and/or otherwise cause the climate control device 116 to cool the environment of the electronic device 100, thereby also cooling the environment of the user 200.

Thus, as shown and described in FIG. 2, once the one or more processors (103) and/or health monitor/heartrate baseline establishment engine (111) detect from signals received from the always on image capture device (105) that a heartrate of the user 200 of the electronic device 100 is rising and passes above the a predefined heartrate threshold, it sends a signal in the form of the climate adjustment request 114 to activate a cooling system, one example of which is the climate control device 116.

Figure 3:
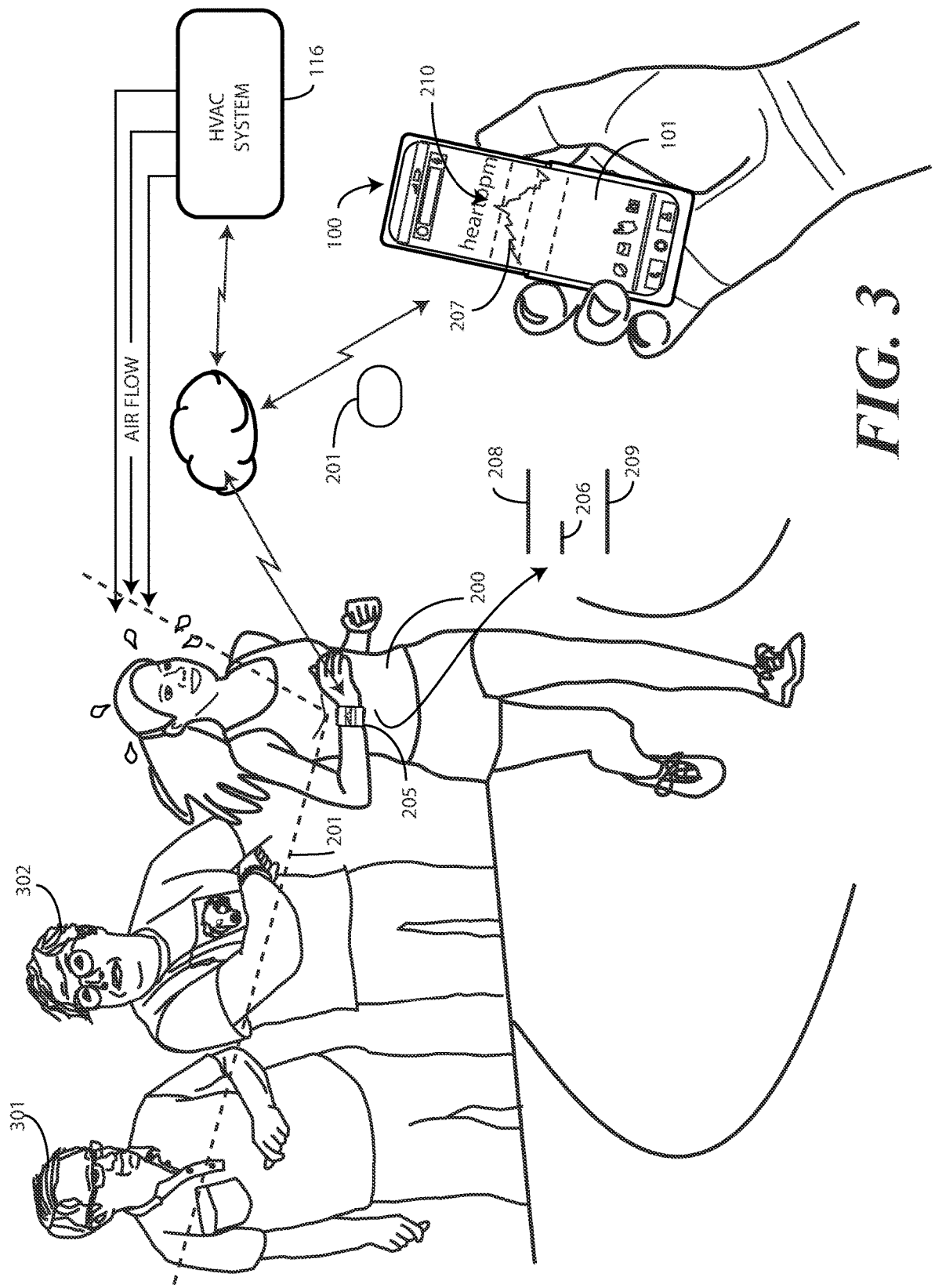
FIG. 3 illustrates one explanatory system in use in accordance with one or more embodiments of the disclosure.

Embodiments of the disclosure contemplate that there will be some instances in which it is desirable to preclude the wireless communication circuit (110) from transmitting the climate adjustment request 114 to the climate control device 116. One of these is shown in FIG. 3. Others will be described below with reference to FIGS. 5-7. Still others will be obvious to those of ordinary skill in the art having the benefit of this disclosure.

Turning first to FIG. 3, illustrated therein is the user 200 of the electronic device 100 exercising in a different environment. Rather than being in a private environment, such as her home, as shown in FIG. 2, in FIG. 3 the user 200 is exercising in a gym where other people are present. Specifically, the user 200 of the electronic device 100 is running on a track with two onlookers 301,302.

As before, an always on image capture device (105) continually monitors the user 200 of the electronic device 100 by capturing a plurality of images 201 of the user 200 of the electronic device 100. In this example, onlooker 302 is the personal trainer of the user 200 of the electronic device 100, while onlooker 301 is her dietician. Since onlooker 302 is the personal trainer, the user 200 of the electronic device 100 has allowed him to hold the electronic device 100 to monitor her heartrate 207 on the display 101. Since the electronic device 100 is not in a position to accurately capture images with the always on image capture device (105) situated within the device itself, it offloads this task to an always on image capture device situated in the smartwatch 205 belonging to the user 200. Accordingly, an always on image capture device in the smartwatch 205 continually monitors the user 200 of the electronic device 100 by capturing the plurality of images 201 of the user 200 of the electronic device 100. The smartwatch 205 then transmits those images 201 to the one or more processors (103) and/or health monitor/heartrate baseline establishment engine (111) via the wireless communication circuit (110) across the network 115.

As before, the one or more processors (103) and/or health monitor/heartrate baseline establishment engine (111) determine, from the plurality of images 201 of the user 200 of the electronic device 100 that the heartrate of the user 207 has risen above the resting level heartrate threshold 208 by the predetermined threshold defined by the difference between the upper predefined heartrate threshold and the mean of the resting level heartrate threshold 208. In normal operation, the wireless communication circuit (110) would transmit a climate adjustment request to the climate control device 116 requesting the climate control device 116 reduce the temperature of the environment.

However, in this illustrative example the personal trainer really dislikes air conditioning and believes that the best way to exercise is to just "sweat it out." Embodiments of the disclosure contemplate that there will be many public settings where multiple persons will be detected in the plurality of images 201 captured by the always on image capture device, and that it frequently will be the case that while one person prefers a lower temperature while exercising to cool off, others may prefer higher temperatures. If, for example, the onlookers 301,302 had been doing hot yoga instead of being the dietician and personal trainer of the user 200, they may have become royally annoyed if the user 200 had unilateral control to turn down the temperature of the climate control device 116. Accordingly, in one or more embodiments the one or more processors (103) preclude transmission of the climate adjustment request to the climate control device 116 when the images 201 of the face and the torso of the user 200 of the electronic device 100 also include depictions of a person other than the user 200 of the electronic device 100. In this example, since the images 201 captured by the always on image capture device of the smartwatch 205, which are transmitted to the one or more processors (103) and/or health monitor/heartrate baseline establishment engine (111), include depictions of the onlookers 301,302, the one or more processors (103) preclude transmission of the climate adjustment request to the climate control device 116. As noted above, other reasons why the one or more processors (103) may preclude transmission of the climate adjustment request to the climate control device 116 will be described below with reference to FIG. 6.

Figure 4:
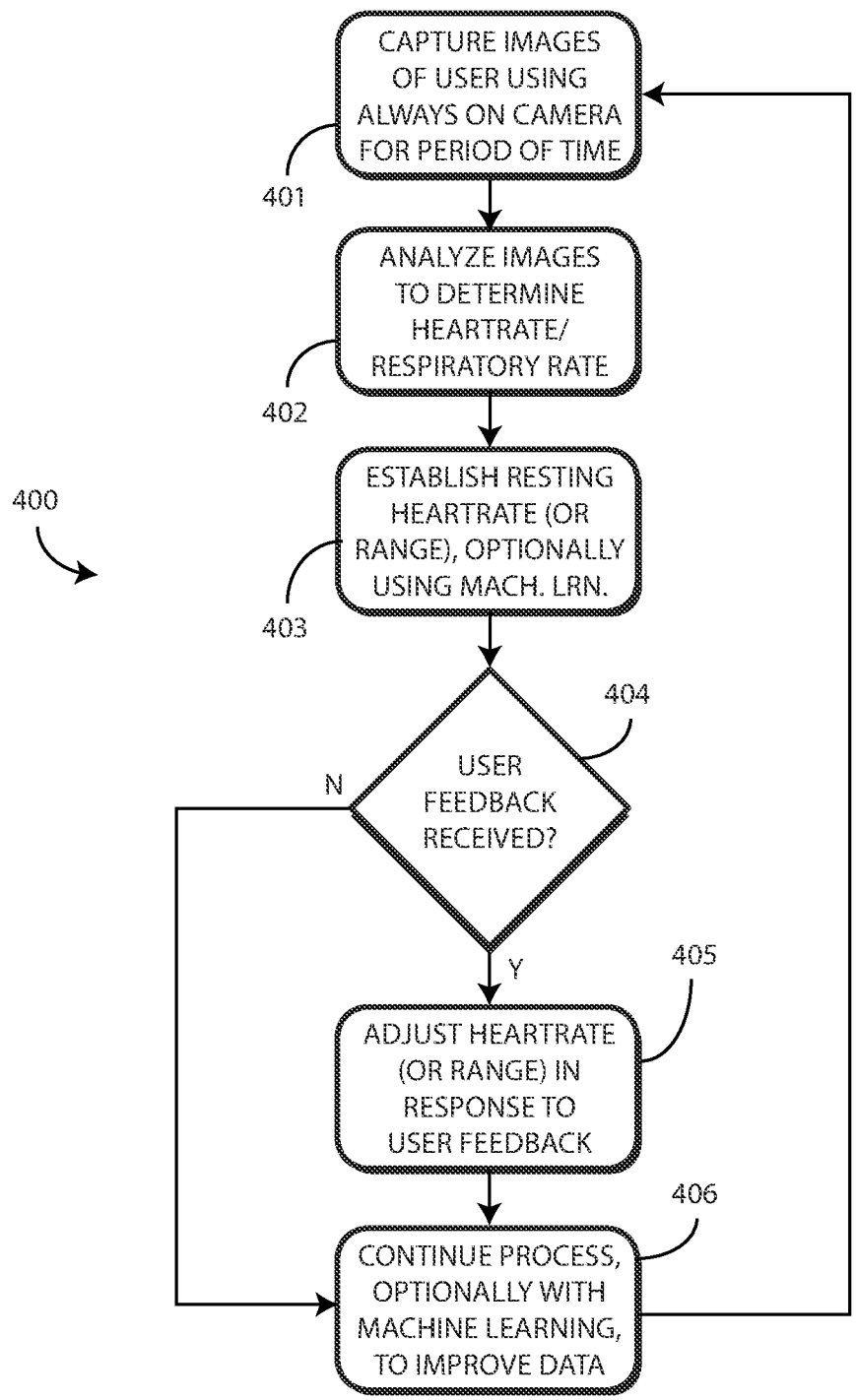
FIG. 4 illustrates one explanatory method in accordance with one or more embodiments of the disclosure.

Turning now to FIG. 4, illustrated therein is one explanatory method 400 of establishing a resting level heartrate of a user of an electronic device in accordance with one or more embodiments of the disclosure. Beginning at step 401, an always on image capture device of the electronic device captures images of the face and/or torso of the user of the electronic device across a period of time. The period of time may be a few days, a few weeks, or a few months or more. Additionally, the period of time may be a sliding window such that a running average of images is always available.

At step 402, one or more processors and/or a health monitor/heartrate baseline establishment engine analyze the images to detect the heartrate of the user. The one or more processors and/or health monitor/heartrate baseline establishment engine can also analyze the images to detect respiratory rate. In one or more embodiments, the one or more processors and/or health monitor/heartrate baseline establishment engine do this by analyzing subtle changes in the depictions of the user of the electronic device to detect shrinking and expansion of blood vessels in the face and torso. The one or more processors and/or health monitor/heartrate baseline establishment engine can also measure color changes in the vessels to detect both heart rate and respiratory rate.

At step 403, the one or more processors and/or health monitor/heartrate baseline establishment engine establish the resting level heartrate by detecting when these heartbeats and/or respiratory breaths are at their lowest levels. These lowest levels are considered to be the resting level heartrate or resting level respiratory rate and can be averaged across time to establish the resting level heartrate and/or resting level respiratory rate. These baselines can be determined using machine learning processes. As previously described, either rate can be defined by a range as well. These results can also be presented to a user of the electronic device as shown above in FIGS. 2 and 3.

Decision 404 then determines whether any user feedback is received in response to establishment of the resting level heartrate or resting level respiratory rate. Illustrating by example, if a user sees that data from last night was used in the computation of the resting level heartrate, and the user had just eaten a sixty-four-ounce porterhouse steak, the user might elect to eliminate that data from the resting level heartrate computation due to the fact that her digestive track was in hyper overdrive trying to digest all that protein. Accordingly, she may deliver user input to excise that data from the computation. She may also replace that data with other data that was captured at the end of a vegan meal where her body was easily digesting miso soup and a tofu scramble. Decision 404 determines if such user feedback is received.

Where it is, step 405 adjusts the resting level heartrate and/or resting level respiratory rate in response to the user feedback. Step 406 then continues the process to refine and improve the accuracy of the resting level heartrate and/or resting level respiratory rate, optionally using machine learning processes. Step 406 can comprise the one or more processors determining the resting level heartrate using a machine learning algorithm monitoring the other images of the face and the torso of the user of the electronic device captured by the image capture device across a predetermined period of time in one or more embodiments.

Figure 5:
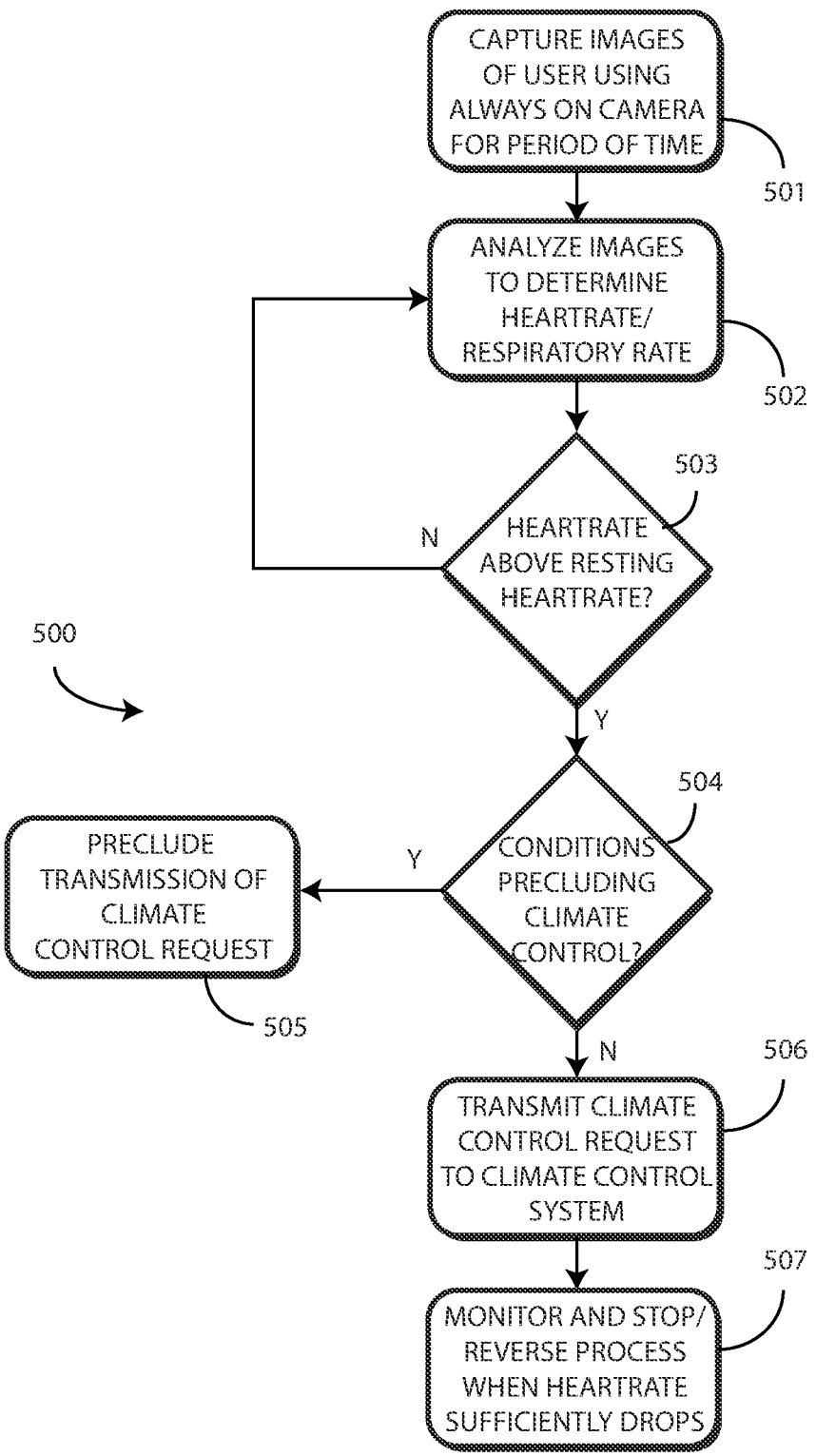
FIG. 5 illustrates another explanatory method in accordance with one or more embodiments of the disclosure.

Turning now tot FIG. 5, illustrated therein is one explanatory method 500 of optically monitoring the heartrate of a user of an electronic device once the baseline has been established by the method (400) of FIG. 4. While heartrate is used for illustrative purposes in the description of the method 500 of FIG. 5 below, respiratory rate can be measured in the same manner.

Beginning at step 501, an always on image capture device captures a plurality of images of a user's face and/or torso across a period of time. At step 502, one or more processors and/or health monitor/heartrate baseline establishment engine determine from the images of the face and/or torso of the user an actively occurring heartrate of the user of the electronic device.

Figure 6:
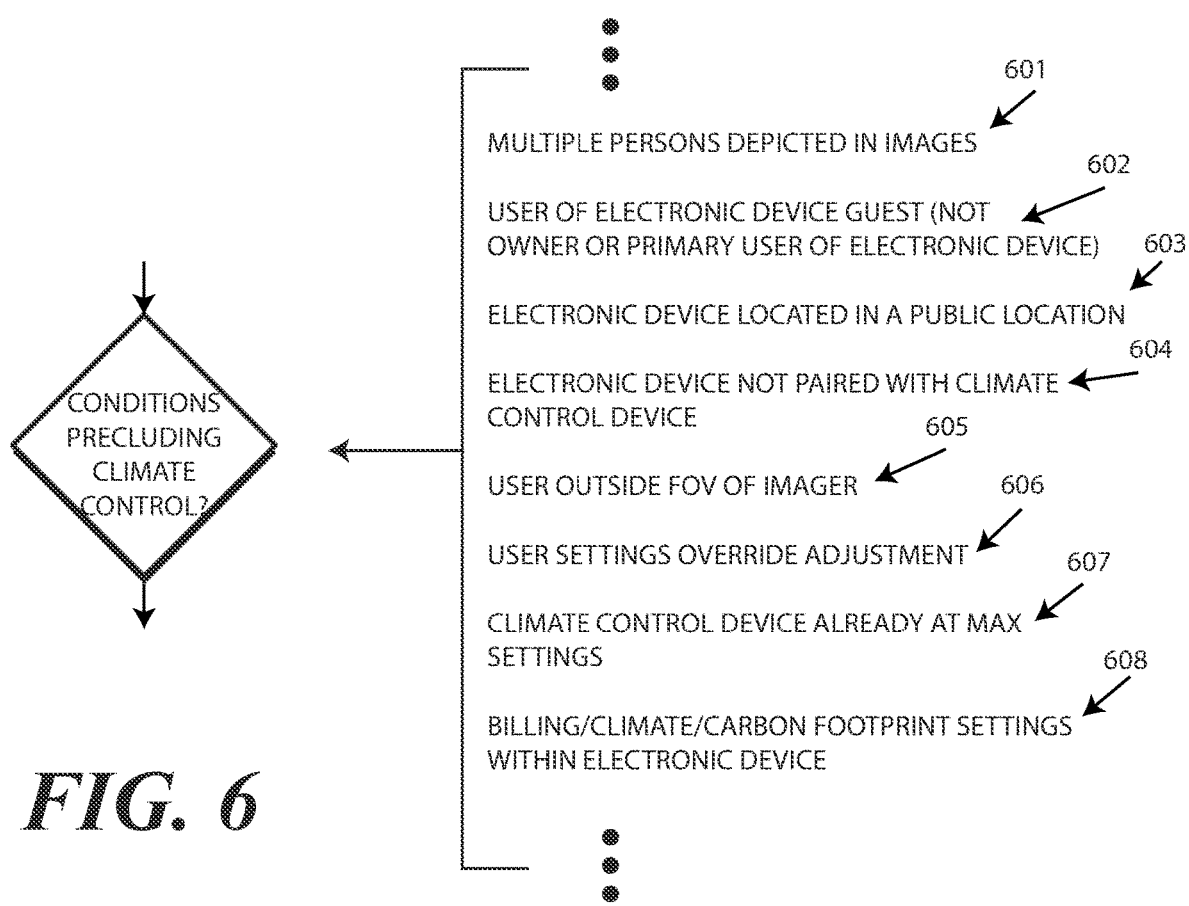
FIG. 6 illustrates one or more conditions that may preclude one or more method steps in accordance with one or more embodiments of the disclosure.

Decision 503 determines, from the images of the face and/or torso whether the heartrate of the user increases by a predetermined threshold above a resting level heartrate of the user of the electronic device. Where it does not, the monitoring of step 502 continues.

Where the heartrate of the user has increased by the predetermined threshold above the resting level heartrate as determined by decision 503, decision 504 determines whether there are any conditions that would preclude the method 500 from making adjustments to a climate control device. Turning briefly to FIG. 6, illustrated therein are several conditions that, where present, may cause such a preclusion.

The first condition 601 was described above with reference to FIG. 3 and occurs in the situation where the plurality of images captured by the always on image capture device depict more than one person. This may indicate that the user of the electronic device is in a public place, and common courtesy may dictate that it is undesirable to allow one person to monopolize control of the air conditioner. Accordingly, one or more processors of an electronic device may preclude transmission of a climate adjustment request to a climate control device when the images of the face and the torso of the user of the electronic device include depictions of a person other than the user of the electronic device.

Another condition 602 that may preclude the transmission of the climate adjustment request is when the person depicted in the images captured by the always on image capture device is not an authorized user of the electronic device. Illustrating by example, consider the situation where an owner of an electronic device configured in accordance with embodiments of the disclosure allows their body-building workout-aholic nephew to come and stay in their home. Seeing the cool new electronic device, the owner may allow the nephew to try out the electronic device while exercising. However, given the nephew's propensity to work out ten hours a day, the owner of the electronic device may not want their HVAC system cycling ON for that much time during the day. Accordingly, in one or more embodiments one or more processors of an electronic device may preclude transmission of a climate adjustment request to a climate control device when someone other than the authorized user of the electronic device is depicted in the images captured by the always on image capture device.

A third condition 603 that may preclude transmission of the climate adjustment request occurs when the electronic device is situated in a public location. A gym owner may not want clients all sending conflicting signals to his expensive, industrial HVAC equipment. Accordingly, in one or more embodiments the electronic device is equipped with a geo-locator allowing the one or more processors to determine whether the electronic device is in a public location, e.g., a mall or public gym, or a private location, e.g., a person's private residence. In one or more embodiments one or more processors of an electronic device may preclude transmission of a climate adjustment request to a climate control device when the electronic device is situated in a public location.

Another condition 604 that may preclude the transmission of the climate adjustment request occurs when there is no climate control device in communication with the wireless communication circuit of the electronic device. Since there is no paired climate control device, there is no reason to transmit the climate adjustment request. Accordingly, in one or more embodiments one or more processors of an electronic device may preclude transmission of a climate adjustment request to a climate control device when there is no climate control device in communication with the wireless communication circuit.

Another condition 605 that may preclude the transmission of the climate adjustment request occurs when no person is within a field of view of the always on image capture device. Embodiments of the disclosure contemplate that the one or more processors may detect the heartrate of the user exceeding a predetermined threshold above the resting level heartrate due to the fact that the person is exercising or undergoing other activities that make their temperature rise. At the same time, this may make the user of the electronic device feel hot. If, for example, the user decides to stop exercising and instead goes to take a shower when the one or more processors detect the heartrate of the user exceeding the predetermined threshold above the resting level heartrate, there is no need to adjust a climate control device because the user is cooling themself via the shower. Accordingly, in one or more embodiments one or more processors of an electronic device may preclude transmission of a climate adjustment request to a climate control device when the user of the electronic device is not within a field of view of the always on image capture device. Said differently, in one or more embodiments the one or more processors cause the wearable communication device to transmit the climate adjustment request only when the user of the electronic device, and optionally an authorized user of the electronic device, is within the field of view of the always on image capture device.

A sixth condition 606 that may preclude the one or more processors from causing the wireless communication circuit to transmit the climate adjustment request are one or more user settings. Embodiments of the disclosure contemplate that the user may be engaged in an activity where they do not want the climate control device to adjust the temperature at all. Hot yoga is one such example where—despite an increased heartrate and profuse sweating—the user of the electronic device may not want the temperature decrease at all. Accordingly, in one or more embodiments one or more processors of an electronic device may preclude transmission of a climate adjustment request to a climate control device when user settings dictate that the temperature should not be altered.

A seventh condition 607 that may preclude the transmission of the climate adjustment request is when the climate control device is already at its maximum settings. Embodiments of the disclosure contemplate that the climate control device with which the wireless communication circuit of the electronic device is in communication could be just a simple fan. Moreover, the fan may be at its highest setting already. Accordingly, one or more processors of an electronic device may preclude transmission of a climate adjustment request to a climate control device when the climate control device is already at its maximum settings.

Yet another condition 608 that may preclude transmission of the climate adjustment request are a user's environmental preferences. A user interested in preventing climate change or staying within a monthly budget may want their HVAC system to run less than a predefined amount of time per month. In one or more embodiments, user settings can be set using a menu that allow maximum greenhouse emissions or run time to be established. These can be subdivided by day. In one or more embodiments one or more processors of an electronic device may preclude transmission of a climate adjustment request to a climate control device when billing, climate, or carbon footprint settings stored within the electronic device indicate that additional operation of the climate control device will exceed these settings. Again, the conditions of FIG. 6 are illustrative only, as numerous others will be obvious to those of ordinary skill in the art having the benefit of this disclosure.

Turning now back to FIG. 5, if any of the conditions preclude the transmission of the climate adjustment request, the same occurs at step 505. Otherwise, at step 506 and in response to determining from the images of the face and/or torso of the user of the electronic device captured by the always on image capture device that the heartrate of the user has increased by a predetermined threshold above the resting level heartrate as determined by decision 503, a wireless communication circuit transmits a climate adjustment request to a climate control device. In one or more embodiments, the climate control device comprises a fan or air conditioner or other cooling device and the climate adjustment request comprises a request to reduce a temperature of an environment of the electronic device.

At step 507, the process can continue. In one or more embodiments, step 507 comprises further determining that the heartrate of the user of the electronic device falls to the resting level heartrate. In response, step 507 can comprise causing the wireless communication circuit to transmit another climate adjustment request to the climate control device requesting that the temperature of the environment of the electronic device return to a level existing before wireless communication circuit transmitted the initial climate adjustment request. In one or more embodiments, step 507 comprises determining that the heartrate of the user of the electronic device falls below the resting level heartrate of the user of the electronic device and, in response, causing the wireless communication circuit to transmit another climate adjustment request to the climate control device comprising a request to increase the temperature of the environment of the electronic device.

The method 500 of FIG. 5 can operate where one or more processors of an electronic device comprising an always on image capture device detect an environment where a wireless communication circuit of the electronic device is in communication with one or more Internet of Things HVAC systems or climate control devices. At step 501, the always on image capture device monitors—in a "touchless" manner without requiring any contact with the user—the user's face and torso. Using the always on image capture device, the one or more processors can continually track the user's resting level heartrate to establish a baseline in accordance with the method (400) of FIG. 4. Respiratory rates can be monitored in a similar manner.

In one or more embodiments, in response to the one or more processors determining that the heartrate of the user has increased by a predetermined threshold above the resting level heartrate at decision 503, the one or more processors cause the wireless communication circuit to send a climate adjustment request to an Internet of Things climate control device at step 506 provided no conditions preclude the same. In one or more embodiments, the climate adjustment request requests that the Internet of Things climate control device reduce the temperature of the environment of the user. In one or more embodiments, this decrease in temperature continues until the one or more processors cause the wireless communication circuit to send another climate adjustment request requesting the temperature return to the user's preferred normal level in response to the one or more processors determining the heartrate of the user has returned to within a predefined range of the resting level heartrate at step 507.

Figure 7:
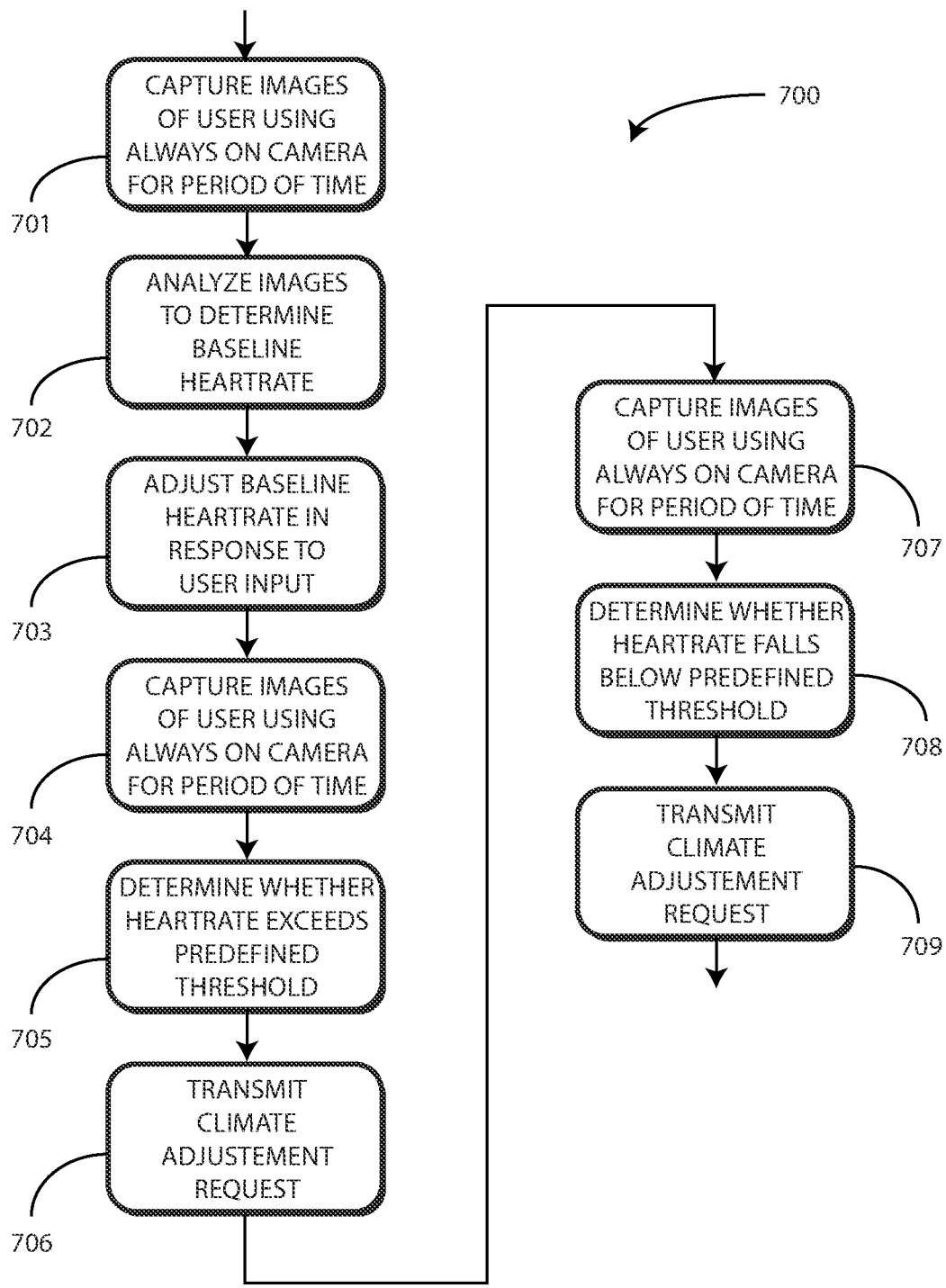
FIG. 7 illustrates still another method in accordance with one or more embodiments of the disclosure

Turning now to FIG. 7, illustrated therein is yet another method 700 in accordance with one or more embodiments of the disclosure. Beginning at step 701, an always on image capture device of an electronic device captures a plurality of images of a user of the electronic device. In one or more embodiments, the plurality of images depicts a face and torso of the user of the electronic device.

At step 702, one or more processors of the electronic device establish a resting level heartrate baseline from the images captured at step 701. In one or more embodiments, the resting level heartrate baseline is defined by an upper resting heartrate threshold and a lower resting heartrate threshold. In one or more embodiments, the one or more processors establish the resting level heartrate baseline at step 702 using machine learning.

At step 703, a user can optionally deliver user input to the one or more processors to adjust the resting level heartrate baseline. Illustrating by example, the user input—where received—can adjust one or both of the upper resting heartrate threshold and/or the lower resting heartrate threshold.

At step 704, an always on image capture device of the electronic device continually monitors the user of the electronic device by capturing a plurality of images of the user of the electronic device. In one or more embodiments, step 704 occurs after the resting level heartrate baseline has been established at step 702.

At step 705, one or more processors determine from the plurality of images captured at step 704 that a heartrate of the user has risen above the resting level heartrate baseline by a predetermined threshold. When this occurs, a wireless communication circuit of the electronic device transmits, in response to the one or more processors determining that the heartrate of the user has risen above the resting level heartrate baseline by the predetermined threshold, a climate adjustment request to a cooling device in communication with the wireless communication circuit at step 706. In one or more embodiments, the climate adjustment request actuates the cooling device to reduce a temperature of an environment of the electronic device.

At step 707, the always on image capture device continues to monitor the user of the electronic device after the wireless communication circuit transmits the climate adjustment request across a local area network to the cooling device at step 706. In one or more embodiments, step 707 comprises the always on image capture device capturing another plurality of images of the user of the electronic device.

At step 708, one or more processors of the electronic device determine from the other plurality of images captured at step 707 that the heartrate of the user has fallen to the resting level heartrate baseline. In one or more embodiments, this determination occurs at step 708 in response to the temperature of the environment of the electronic device having been reduced. Accordingly, at step 709, the wireless communication circuit of the electronic device transmits, in response to the one or more processors determining that the heartrate of the user has fallen to the resting level heartrate baseline at step 708, another climate adjustment request across the local area network to the cooling device in communication with the wireless communication circuit. In one or more embodiments this other climate adjustment request deactuates the cooling device to preclude further reduction of the temperature of the environment of the electronic device. The method 700 can then repeat as necessary.

Figure 8:
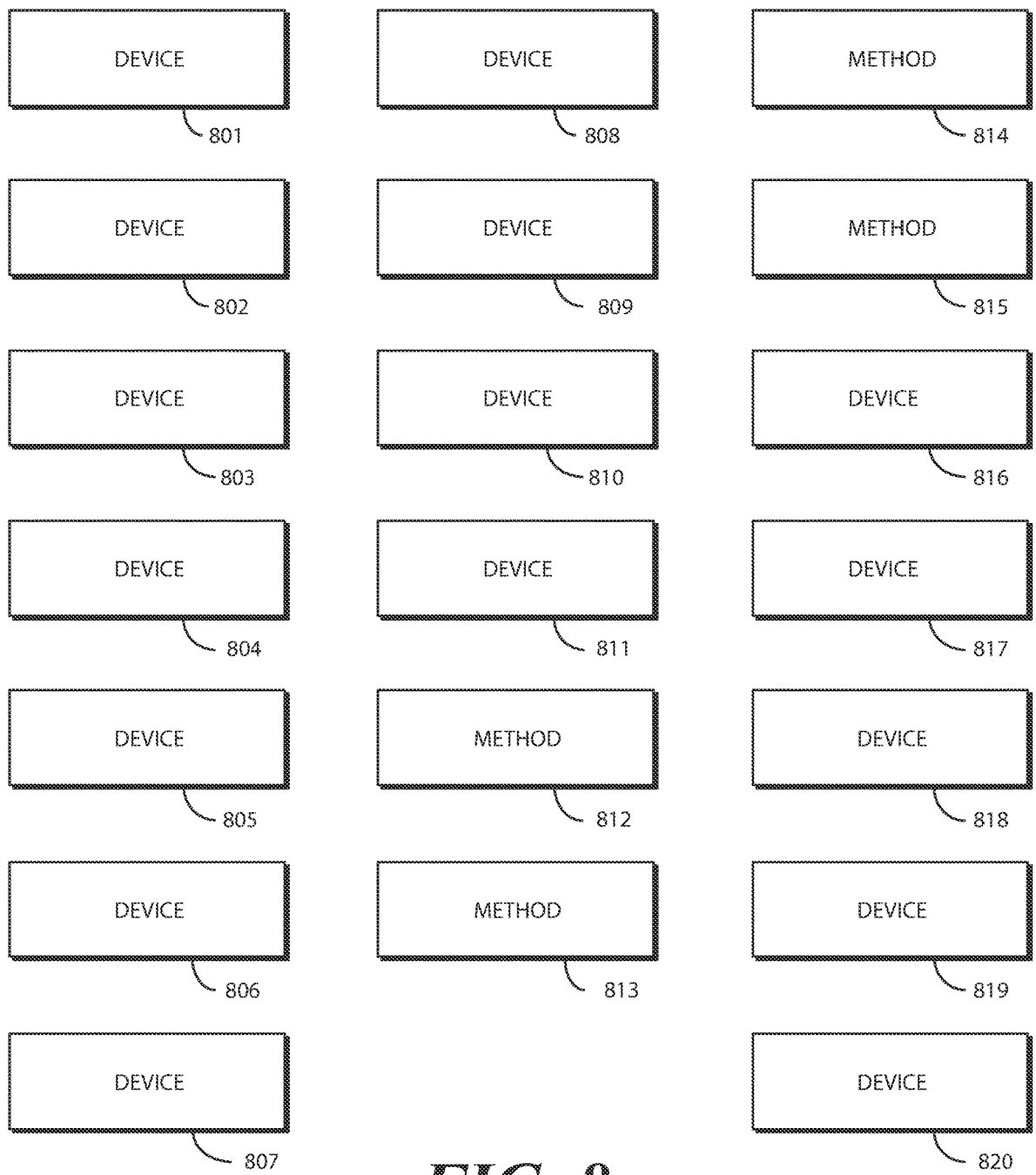
FIG. 8 illustrates various embodiments of the disclosure.

Turning now to FIG. 8, illustrated therein are various embodiments of the disclosure. The embodiments of FIG. 8 are shown as labeled boxes in FIG. 8 due to the fact that the individual components of these embodiments have been illustrated in detail in FIGS. 1-7, which precede FIG. 8. Accordingly, since these items have previously been illustrated and described their repeated illustration is no longer essential for a proper understanding of these embodiments. Thus, the embodiments are shown as labeled boxes.

At 801, an electronic device comprises an image capture device and one or more processors operable with the image capture device. At 801, the electronic device comprises a wireless communication circuit operable with the one or more processors.

At 801, the one or more processors determine, from images of a face and torso of a user of the electronic device captured by the image capture device, that a heartrate of the user of the electronic device increases by a predetermined threshold above a resting level heartrate of the user of the electronic device. At 801, in response to the heartrate increasing by the predetermined threshold above the resting level heartrate, the one or more processors cause the wireless communication circuit to transmit a climate adjustment request to a climate control device.

At 802, the image capture device of 801 comprises an always-on image capture device. At 803, the climate control device of 802 comprises one of a fan or an air conditioner. At 803, the climate adjustment request comprises a request to reduce a temperature of an environment of the electronic device.

At 804, the one or more processors of 803 determine that the heartrate of the user of the electronic device falls to the resting level heartrate of the user of the electronic device. At 804, in response, the one or more processors cause the wireless communication circuit to transmit another climate adjustment request to the climate control device. At 804, the other climate adjustment request requests the temperature of the environment of the electronic device return to a level existing before the one or more processors caused the wireless communication circuit to transmit the climate adjustment request.

At 805, the images of the face and torso of the user captured at 804 are captured by the image capture device while the device is in a low-power or sleep mode of operation. At 806, the one or more processors of 804 determine the resting level heartrate from other images of the face and the torso of the user of the electronic device captured by the image capture device.

At 807, the one or more processors of 806 determine the resting level heartrate using a machine learning algorithm monitoring the other images of the face and the torso of the user of the electronic device captured by the image capture device across a predetermined period of time. At 808, the resting level heartrate of 807 is defined by a predefined upper resting heartrate threshold and a predefined lower resting heartrate threshold.

At 809, the one or more processors of 803 further determine that the heartrate of the user of the electronic device falls below the resting level heartrate of the user of the electronic device and, in response, cause the wireless communication circuit to transmit another climate adjustment request to the climate control device comprising a request to increase the temperature of the environment of the electronic device.

At 810, the one or more processors of 801 preclude transmission of the climate adjustment request to the climate control device when the images of the face and the torso of the user of the electronic device include depictions of a person other than the user of the electronic device. At 811, the one or more processors of 801 cause the wireless communication circuit to transmit the climate adjustment request to the climate control device only when the user of the electronic device is within a field of view of the image capture device.

At 812, a method in an electronic device comprises detecting, with an always-on image capture device of an electronic device monitoring a user of the electronic device by capturing a plurality of successive images of the user of the electronic device, a heartrate of the user of the electronic device being above a predefined heartrate threshold. At 812, the method comprises causing, with one or more processors, when the heartrate is above the predefined heartrate threshold, a wireless communication circuit to transmit a climate adjustment request to a climate control device requesting that a temperature of an environment of the electronic device decrease.

At 813, the method of 812 further comprises causing the wireless communication circuit to deliver a heartrate elevation occurrence across a network to a companion electronic device. At 184, the method of 812 further comprises establishing, with the one or more processors, a resting heartrate of the user of the electronic device by causing the always-on image capture device to capture a series of images of the user of the electronic device across a predefined amount of time. At 815, the method of 812 further comprises detecting, with the one or more processors, a respiratory rate of the user of the electronic device from the plurality of successive images of the user of the electronic device.

At 816, an electronic device comprises an always-on image capture device continually monitoring a user of the electronic device by capturing a plurality of images of the user of the electronic device. At 816, the electronic device comprises one or more processors determining, from the plurality of images of the user of the electronic device that a heartrate of the user has risen above a resting heartrate by a predefined threshold.

At 816, the electronic device comprises a wireless communication circuit transmitting, in response to the one or more processors determining that the heartrate of the user has risen above the resting heartrate by the predefined threshold, a climate adjustment request across a local area network to a cooling device in communication with the wireless communication circuit. At 816, the climate adjustment request actuates the cooling device to reduce a temperature of an environment of the electronic device.

At 817, the always on image capture device of 816 continues to monitor the user of the electronic device after the wireless communication circuit transmits the climate adjustment request across the local area network to the cooling device by capturing another plurality of images of the user of the electronic device. At 817, the one or more processors determine, from the other plurality of images of the user of the electronic device that the heartrate of the user has fallen to the resting heartrate in response to the temperature of the environment of the electronic device being reduced.

At 817, the wireless communication circuit transmits, in response to the one or more processors determining that the heartrate of the user has fallen to the resting heartrate by the predefined threshold, another climate adjustment request across the local area network to the cooling device in communication with the wireless communication circuit. At 817, the other climate adjustment request deactivates the cooling device to preclude further reduction of the temperature of the environment of the electronic device.

At 818, one or both of the plurality of images of the user of the electronic device or the other plurality of images of the user of the electronic device of 817 depict a face and torso of the user of the electronic device. At 819, the resting heartrate of 818 is defined by an upper resting heartrate threshold and a lower resting heartrate threshold established by machine learning.

At 820, the electronic device of 819 further comprises a user interface. At 820, the one or more processors receive user input from the user interface. At 820, the one or more processors adjusting one or both of the upper resting heartrate threshold and/or the lower resting heartrate threshold as a function of the user input.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims.

For example, while illustrative examples transmit climate adjustment requests to climate control devices to cool an environment of an electronic device in response to a heartrate of the user exceeding a predefined threshold above a resting level heartrate, embodiments of the disclosure can work in other ways as well. For instance, in response to the one or more processors determining that the heartrate of the user has decreased by a predetermined threshold below the resting level heartrate (these determinations can be made via machine learning across a predefined period of time), the one or more processors cause the wireless communication circuit to send another climate adjustment request to the climate control device to increase the ambient temperature. As such, embodiments of the disclosure can be used to warm the environment in addition to cooling.

Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. An electronic device, comprising:
   an image capture device comprising an imager configured to capture one or more images from an environment of the electronic device;
   one or more processors operable with the image capture device; and
   a wireless communication circuit operable with the one or more processors;
   the one or more processors determining, from images of a face and torso of a user of the electronic device captured by the image capture device, that a heartrate of the user of the electronic device increases by a predetermined threshold above a resting level heartrate of the user of the electronic device and, in response to the heartrate increasing by the predetermined threshold above the resting level heartrate, causing the wireless communication circuit to transmit a climate adjustment request to a climate control device operable to alter an ambient temperature of an environment of the electronic device;
   the image capture device comprising an always-on image capture device;
   the climate control device comprising one of a fan or an air conditioner, the climate adjustment request comprising a request to reduce a temperature of an environment of the electronic device; and
   the one or more processors further determining that the heartrate of the user of the electronic device falls to the resting level heartrate of the user of the electronic device and, in response, causing the wireless communication circuit to transmit another climate adjustment request to the climate control device requesting the temperature of the environment of the electronic device return to a level existing before the one or more processors caused the wireless communication circuit to transmit the climate adjustment request.

2. The device of claim 1, wherein the one or more processors determine the heartrate of the user by one or more of detecting shrinking and expansion of blood vessels depicted in the one or more images or by measuring color changes of blood vessels depicted in the one or more images.

3. The device of claim 1, wherein the one or more processors establish the resting level heartrate of the user by detecting when the heartrate of the user is at its lowest level when averaged across time.

4. The device of claim 1, further comprising a user interface, the one or more processors further presenting one or both of the heartrate of the user and/or the resting level heartrate of the user on the user interface of the electronic device.

5. The device of claim 1, wherein the one or more images of the face and the torso of the user of the electronic device are captured by the image capture device while the device is in a low-power or sleep mode of operation.

6. The device of claim 1, the one or more processors determining the resting level heartrate from other images of the face and the torso of the user of the electronic device captured by the image capture device.

7. The device of claim 6, the one or more processors determining the resting level heartrate using a machine learning algorithm monitoring the other images of the face and the torso of the user of the electronic device captured by the image capture device across a predetermined period of time.

8. The device of claim 7, the resting level heartrate defined by a predefined upper resting heartrate threshold and a predefined lower resting heartrate threshold.

9. The device of claim 1, the one or more processors further determining that the heartrate of the user of the electronic device falls below the resting level heartrate of the user of the electronic device and, in response, causing the wireless communication circuit to transmit an additional climate adjustment request to the climate control device comprising a request to increase the temperature of the environment of the electronic device.

10. The device of claim 1, the one or more processors precluding transmission of the climate adjustment request to the climate control device when the images of the face and the torso of the user of the electronic device include depictions of a person other than the user of the electronic device.

11. The device of claim 1, the one or more processors causing the wireless communication circuit to transmit the climate adjustment request to the climate control device only when the user of the electronic device is within a field of view of the image capture device.

12. The device of claim 1, further comprising a user interface operable with the one or more processors, the one or more processors further receiving user feedback from the user interface and adjusting the resting level heartrate in response to the user feedback.

13. The device of claim 1, the one or more processors further operable to transmit the heartrate of the user to a companion electronic device.

14. An electronic device, comprising:
an always-on image capture device that remains active without transitioning to a sleep mode and comprising an imager configured to capture one or more images from an environment to the electronic device and continually monitoring a user of the electronic device by capturing a plurality of images of the user of the electronic device;
one or more processors determining, from the plurality of images of the user of the electronic device that a heartrate of the user has risen above a resting heartrate by a predefined threshold; and
a wireless communication circuit transmitting, in response to the one or more processors determining that the heartrate of the user has risen above the resting heartrate by the predefined threshold, a climate adjustment request across a local area network to a cooling device in communication with the wireless communication circuit;
wherein:
the climate adjustment request actuates the cooling device to reduce a temperature of an environment of the electronic device;
the always-on image capture device continues to monitor the user of the electronic device after the wireless communication circuit transmits the climate adjustment request across the local area network to the cooling device by capturing another plurality of images of the user of the electronic device;
one or more processors determine, from the another plurality of images of the user of the electronic device that the heartrate of the user has fallen to the resting heartrate in response to the temperature of the environment of the electronic device being reduced; and
the wireless communication circuit transmits, in response to the one or more processors determining that the heartrate of the user has fallen to the resting heartrate by the predefined threshold, another climate adjustment request across the local area network to the cooling device in communication with the wireless communication circuit; and
the another climate adjustment request deactuates the cooling device to preclude further reduction of the temperature of the environment of the electronic device.

15. The device of claim 14, wherein the cooling device comprising one of a fan or an air conditioner.

16. The device of claim 14, wherein one or both of the plurality of images of the user of the electronic device or the another plurality of images of the user of the electronic device depicts a face and torso of the user of the electronic device.

17. The device of claim 16, wherein the resting heartrate is defined by an upper resting heartrate threshold and a lower resting heartrate threshold established by machine learning.

18. The device of claim 17, further comprising a user interface, the one or more processors receiving user input from the user interface, the one or more processors adjusting one or both of the upper resting heartrate threshold and/or the lower resting heartrate threshold as a function of the user input.

19. The device of claim 13, the one or more processors further operable to transmit the resting level heartrate to the companion electronic device.

20. The device of claim 19, wherein the companion electronic device is one of a tablet computer or a smartwatch.

* * * * *